United States Patent [19]

Narayanan

[11] Patent Number: 5,425,955

[45] Date of Patent: Jun. 20, 1995

[54] COMPOSITIONS OF INSOLUBLE FILM-FORMING POLYMERS AND USES THEREFOR

[75] Inventor: Kolazi S. Narayanan, Palisades Park, N.J.

[73] Assignee: ISP Investments Inc., Wilmington, Del.

[21] Appl. No.: 17,093

[22] Filed: Feb. 12, 1993

Related U.S. Application Data

[63] Continuation-in-part of Ser. No. 975,811, Nov. 13, 1992.

[51] Int. Cl.[6] .................... A01N 25/04; A01N 25/14; A61K 9/10; A61K 9/107
[52] U.S. Cl. .................................. 424/405; 424/407; 424/409; 71/64.02; 71/64.1; 71/DIG 1; 523/122; 514/937; 514/938
[58] Field of Search .................... 514/772.5, 937, 938; 424/405, 407, 409; 71/64.02, 64.1, DIG 1

[56] References Cited

U.S. PATENT DOCUMENTS

| | | | |
|---|---|---|---|
| 4,482,534 | 11/1984 | Blank | 424/449 |
| 5,061,751 | 10/1991 | Patton | 524/33 |
| 5,093,031 | 3/1992 | Login et al. | 548/529 |

*Primary Examiner*—Edward J. Webman
*Attorney, Agent, or Firm*—Jules E. Goldberg; Joshua J. Ward

[57] ABSTRACT

Emulsion concentrates of water-insoluble film-forming polymers are disclosed which can be utilized to form water-resistant films of active ingredients, such as, agriculturally active chemicals. Methods for preparation and use of the emulsion concentrates are disclosed.

16 Claims, No Drawings

COMPOSITIONS OF INSOLUBLE FILM-FORMING POLYMERS AND USES THEREFOR

CROSS-REFERENCE TO RELATED APPLICATIONS

This application is a continuation-in-part of application Ser. No. 07/975,811, filed Nov. 13, 1992, the contents of which are incorporated herein by reference.

BACKGROUND OF THE INVENTION

Certain types of polymers exhibit film-forming properties and when dissolved in an organic solvent, can be applied for the purpose of providing a water-resistant coating on a substrate. Usually, the film-forming polymer in the solvent is applied to the particular substrate to be coated, and the solvent is allowed to evaporate or removed leaving a film of the polymer.

Generally, however, such water-resistant, film-forming polymers are soluble only in organic solvents, i.e., they are substantially insoluble in water. The use of such organic solvents generally is undesirable since they exhibit environmentally adverse properties, are often hazardous or flammable, and are generally expensive. In order to avoid the environmentally adverse effects of such organic solvents as well as to reduce the cost involved with using such solvents, rather complicated solvent recovery procedures must be used.

Typical of such polymers are copolymers of N-vinylpyrrolidone with α-olefins, vinyl acetate, styrene, acrylates, acrylic acids, amides, maleic acid, mono and diesters of maleic acids, and the like.

In parent application Ser. No. 07/975,811, a method is disclosed for providing a stable microemulsion of a particular class of water-insoluble film-forming polymers in water. The microemulsions thus formed, can be utilized to produce films of the particular film-forming polymer on a given substrate. For example, the microemulsion can be used as a coating for substrates, such as, wood, metal, glass, and the like. In addition, various active ingredients, e.g., fungicides, preservatives, insecticides, insect repellents, pheromones, radiation absorbents, dyes, and the like, can be included in the composition.

The compositions disclosed therein are composed of the water-insoluble polymer, a surfactant, and a long-chain alkylpyrrolidone. The amounts of the polymer surfactant and long-chain alkylpyrrolidone can vary within a broad range. However, the relative compositional ranges of each must be such that a clear, stable microemulsion or solution of the insoluble polymer is obtained on the addition of water.

A significant problem in the use of agriculturally active chemicals is that since they are applied to soil and plant surfaces, they are susceptible to being washed off by rain and/or water spray used for irrigation. This adversely affects the efficiency of the chemicals, since the longer the chemical remains in contact with the plant or soil surface, the more effective it is.

SUMMARY OF THE INVENTION

I have discovered a new class of emulsion concentrates of such water-insoluble film-forming polymers which comprise a water-insoluble polymer, an agriculturally active chemical, and an organic solvent for the agriculturally active chemical. The water-insoluble polymers used in the present invention are graft polymers of vinylpyrrolidone and α-olefin wherein the N-vinylpyrrolidone is present in more than about 5 percent on a weight basis. Preferably, the weight percent of N-vinyl pyrrolidone is at least about 10 percent. The α-olefin should contain from 8 to 30, and preferably, from 16 to 20 carbon atoms.

The inventive compositions are particularly convenient for use with oil-based concentrates, e.g., commercial Prowl, Fusilade, and Thiadiazuron. However, they can also be used in aqueous-based hydrophobic active ingredients, e.g., aqueous emulsions or dispersions of carbaryl (Sevin).

The emulsion concentrate of the present invention provides a stable emulsion upon dilution with water. Thus, the emulsion concentrate of the invention is particularly suitable for use with an agriculturally active chemical or ingredient (hereinafter, sometimes referred to as a.i.). The diluted inventive concentrate of the film-forming polymer may include an agriculturally active chemical or ingredient, such as, pesticides, herbicides, and the like. This composition may then be applied to plants, or soil, in the usual manner. I have found that the inventive composition, thus used, forms a film incorporating the a.i. on the leaf, soil or seeds and can prevent wash-out of the agriculturally active ingredient due to rain. Thus, for example, the composition with an agriculturally active ingredient forms a film on the particular substrate, e.g., the plant or soil, which results in improved retention and enhanced bioactivity of the agriculturally active ingredient and also provides superior rainfastness for such ingredients on leaf and substrate surfaces.

DETAILED DESCRIPTION OF THE INVENTION

As used herein, the following terms have the meaning indicated:

"macroemulsion" means an emulsion of water-in-oil or oil-in-water wherein the interior phase is in the form of visually discernable droplets and the overall emulsion is cloudy, and wherein the droplet diameter is greater than about 1 micron, and usually greater than about 10 microns.

"microemulsion" means an oil-in-water or water-in-oil, transparent thermodynamically stable dispersion of two or more immiscible liquids or a solid in a liquid wherein the dispersed phase consists of small droplets with diameters in the range of about 10 to 100 millimicrons. Such microemulsions are clear and appear as a single phase to the naked eye.

"single phase" as applied to a liquid means that to the naked eye, the liquid is homogeneous and does not appear to contain any other separatable liquid phase.

"clear" or "transparent" as applied to a liquid means that the liquid appears as a single phase without any particulate or colloidal material or a second phase being present when viewed by the naked eye.

"substantially insoluble" or "insoluble" means that for all practical purposes, the solubility of the compound in water is insufficient to make the compound practicably usable in an agricultural end use without some modification either to increase its solubility or dispersability in water, so as to increase the compound's bioavailability or avoid the use of excessively large volumes of solvent.

"High degree of loading in the concentrate" means an agriculturally active ingredient content of at least about 5 percent by weight.

"agriculturally active chemical or ingredient" (AAC or a.i.) means compounds and mixtures thereof which can be used as agricultural fertilizers, nutrients, plant growth accelerants, herbicides, plant growth controlling chemicals, and chemicals which are effective in killing plants, insects, microorganisms, fungi, bacteria and the like which are commonly referred to as insecticides, bactericides, fungicides, nematocides, fumigants, synergists, i.e., compounds which when used in conjunction with other AAC's enhance their activity and the like, as well as any other chemicals having properties which are suitable for agricultural uses in terms of application to plants or domestic uses for controlling insects and pests.

Long-chain N-alkylpyrrolidones suitable for use as a solvent in the present invention have the formula

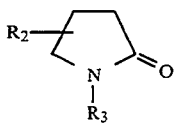

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14. Preferably, $R_2$ is hydrogen and $R_3$ is $C_8$ or $C_{12}$. Mixtures of two long-chain alkylpyrrolidones may also be used. N-methyl pyrrolidone may also be included along with long chain N-alkylpyrrolidones in an amount effective to help maintain the solubility of the long chain alkylpyrrolidones.

The solvent may also be an organic diluent which is a synthetic or naturally occurring oil having a high hydrophobic character or having a fractional dispersive solubility parameter of greater than 70% and preferably greater than 85% and a molar volume of greater than 90 cm$^3$/mole. These properties are defined in the C.R.C. Handbook. Typical diluents include soybean oil, rapeseed oil, long chain alcohols, long chain ketones, long chain esters, and ethers. As used herein, "long chain" means with 6 or more carbon atoms. Also suitable as the organic diluent are aromatic petroleum oils including those which are commercially available distillates from crude oils having an average boiling point greater than 120° C. Typical of such materials are those sold under the trademarks Exxon 200 or Texaco 400. Of course, such aromatics should be approved for use as a carrier for agriculturally active chemicals.

The composition of the aromatic petroleum oil is generally:
Heavy aromatic solvent naphtha—about 60%;
Middle distillate solvent extractant—about 40%;
Normally, these oils contain predominantly the $C_9$-$C_{15}$ aromatic hydrocarbons and primarily the $C_{10}$-$C_{12}$ hydrocarbons having a flash point of about 203° F.

When a surfactant is used, e.g., because of the nature of the active ingredient, the concentration of the active ingredient desired, and the like, suitable surfactants include both water and oil-soluble surfactants, e.g., ethoxylated alkyl phenols, linear aliphatic polyesters, linear aromatic polyesters, polyalkenyloxyalcohol, linear aliphatic ethoxylates, polyethoxylated castor oil, polyethoxylated carboxylates, and polyethoxylated alkylamines. Oil and water-soluble anionic surfactants may be used as the emulsifier and include phosphate esters and their salts, alkyl sulfates, sulfonates, and their salts, salts of sulfate nonylphenoxypoly(ethyleneoxy) ethanol, salts of alkylbenzene sulfonates, e.g., the sodium, calcium and alkylammonium salts, salts of alkylnaphthalene sulfonate, and sulfonated aliphatic polyesters and their salts. Also suitable are complex phosphate esters of nonionic surfactants of the ethylene oxide type which are mixtures of diesters of phosphoric acid. (See, for example, McCutcheon's, *Emulsifiers and detergents* (1989), published by McCutcheon's Division of M.C. Publishing Co., Glen Rock, N.J.)

Polymers particularly suitable for use in the present invention include copolymers of vinyl pyrrolidone and α-olefins. Typically, such α-olefins contain up to 20, and preferably 16, carbon atoms. The weight average molecular weight of such polymers is generally greater than about 10,000. Particularly suitable are water-insoluble polymers, such as, Agrimer AL25 (International Specialty Products (ISP) Corporation), which is a copolymer of an α-olefin having the formula $C_{14}H_{29}CH=CH_2$(50%) and N-vinylpyrrolidone (50%), and Agrimer AL30 (ISP Corporation), which is a copolymer of an α-olefin having 20 carbon atoms (80%), and N-vinylpyrrolidone (20%). Copolymers of N-vinylpyrrolidone and vinyl acetate should contain at least about 10% N-vinylpyrrolidone and have a weight average molecular weight of at least about 10,000.

Typically, the inventive concentrate comprises from about 2 to 90 percent, preferably from 5 to 85, and most preferably, from about 30 to 80 percent by weight solvent, e.g., N-alkyl pyrrolidone, organic diluent or both and from about 1 to 60, and preferably from about 5 to 30 percent, and most preferably, 10 to 25 weight percent of the water insoluble polymer. If a surfactant is present, the amount is from 1 to 85% and, preferably, from 3 to 70 percent, and most preferably, from about 5 to 60 percent by weight.

All percents herein are percent by weight based on the total weight of the composition.

The inventive compositions are particularly suitable for end use applications wherein films of water-insoluble polymers are formed on substrates. The films may be formed for adhesive, protective, decorative, and lubricating, purposes and to impart hydrophobicity or hydrophilicity. Since it is desirable to avoid organic solvents due to their cost and adverse toxicological and environmental properties, the use of water as a solvent for the film-making procedure is preferred. With the inventive composition, it becomes possible to place such ordinarily water-insoluble film-forming polymers in an aqueous based vehicle, i.e., solution, emulsion or dispersion-solubilizing liquid, which can be handled and utilized in the same manner as a true solution of the polymer to form a film therewith. Thus, the inventive composition in microemulsion form may be coated as is, or after further dilution with water, if desired, onto a substrate. The water is then removed as by evaporation to leave the polymer film remaining.

I have further discovered that the rainfastness of agriculturally active ingredients, and in particular, pesticides, can be substantially improved by formulating the pesticides in the inventive composition including the water insoluble film-forming polymer. Thus, many pesticides, and particularly water soluble agriculturally active chemicals, are washed off by rain after they have been applied to the plants or soil. For effective pest and weed control, it takes from a few hours to three weeks for the pesticide to penetrate into the biological system. The present invention assures that the agriculturally active ingredient will be retained for a sufficiently long time to allow it to be effective and avoid or reduce rain wash-off.

In use, the inventive composition is diluted with water and applied to the crop, plants, or soil. Normally, this dilution is carried out at the field site. As used herein, rainfast resistant, rainfast or rainfastness in connection with the inventive compositions means that a film formed from the composition exhibits increased resistance to removal by water washing as compared to the same composition which does not contain the film-forming polymer under the test procedures as described hereinafter.

Pesticides which can be used with the present invention, may be characterized by their physical properties, depending on their physical state at normal or ambient conditions, i.e., between 40° F. and 90° F. and their solubility or miscibility with water or other common organic solvents, e.g., aromatics, such as, toluene, xylene, methylated and polyalkylated naphthalenes, and aliphatic solvents.

Based on the physical properties, the pesticides may be classified into three groups:

The first group includes those which are oily liquids at ambient temperatures and are immiscible with water. Specific pesticides include:

Common esters of 2,4-dichlorophenoxyacetic acid,
Common esters of 2,4,5-trichlorophenoxyacetic acid,
Common esters of 2-(2,4-dichlorophenoxy) propionic acid,
Common esters of 2-(2,4,5-trichlorophenoxy) propionic acid,
Common esters of 2,4-dichlorobutyric acid,
Common esters of 2,methoxy-3,6-dichlorobenzoic acid,
Common esters of 2-methyl-4-chlorophenoxyacetic acid,
Piperonyl butoxide 3,4-methylenedioxy-6-propyl benzyl n-butyl diethylene glycol ether,
Bromophos ethyl: 0,0-diethyl-0-2,5-dichloro-4-bromophenyl thionophosphate,
N-(2-mercaptoethyl) benzene-sulfonamide (BETASAN ®),
Isobornyl Thiocyanoacetate (THANITE ®),
Ioxynil ester of octanoic acid,
Molinate S-ethyl hexahydro-1H-azepine-1-carbothioate,
PP 511 0,0-dimethyl-(2-diethylamine 4-methyl-6-pyrimidinyl) carbamate,
PP 211 0,0-diethyl 0-(2-diethylamine-4-methyl-6-pyrimidinyl) phosphorocarbamate,
5-Ethoxy-3-(trichlorometyl)-1,2,4-thiadiazole (TERRAZALE ®),
Ethyl-s-s-dipropyl-phosphodithioate (MOCAP ®),
S-Ethyl dipropylthiocarbamate (EPTAM ®),
S-Ethyl diisobutylthiocarbamate (SUTAN ®),
S-n. propyl-di-n-propylthiocarbamate (VERNAM ®),
S-propyl butylethylthiocarbamatae (TILLAM ®),
S-ethyl ethylcyclohexylthiocarbamate (RO-NEET ®),
Malathion (S-( 1,2-dicarboxyethyl)-0,0-dimethyl phosphorodithioate),
Diazinon (0,0-diethyl,0-(2-isopropyl-4-methyl-6-pyrimidinyl) phosphorothioate,
-Ethyl-S-phenyl-ethylphosphonodithioate (DYFONATE ®),
Toxaphene (Octachlorocamphene),
Bromoxynil (3,5-dibromo-4-hydroxy benzonitrile ester of n. octanoic acid,
2-chloro-N-2,6-diethylphenyl-N-methoxymethylacetamide (LASSO ®),
Diallate S-2,3-dichloroallyl N,N-diisopropylthiolcarbamate,
Triallate S-2,33-trichloroallyl N,N-diisopropylthiolcarbamate.

The second group comprises those pesticides which are solids at ambient temperatures and for all practical purposes, insoluble in water.

2,4,5-T (2,4,5-trichlorophenoxy acetic acid)
Monuron (3-(p-chlorophenyl)-1,1-dimethyl urea)
Diuron (3-(3,4-dichlorophenyl)-1,1-dimethyl urea)
Bromacil (5-bromo-3-sec. butyl-6-methyl uracil)
Isocil (5-bromo-3-isopropyl-6-methyl uracil)
Linuron (3-(3,4-dichlorophenyl)-1-methoxy-1-methyl urea
Atrazine (2-chloro-4-ethylamino-6-isopropylamino-s-triazine) Simazine (2-chloro-4,6,-bis(ethylamino)-s-triazine
Dodine (n-dodecylguanidine acetate)
Thiram (tetramethylthiuram disulfide)
N-(mercaptomethyl)phthalimide s-(o,o dimethylphosphorodithioate) (IMIDAN ®)
Lindane (gamma 1,2,3,4,5,6 hexachlorocyclohexane)
Folpet (N-trichloromethylphthalimide)
Manazon (s-(4,6-diamino- 1,3,5-triazin-2-yl methyl)-dimethyl phosphorothiolthionate)
Barban (4-chloro-2 butynyl m-chlorocarbanilate)
Tricumba 2-methoxy-3,5,6-trichlorobenzoic acid
Trifluralin (2,6-dinitro-N,N-dipropyl-4-trifluoromethylaniline) (2,3dihydro-5-carboxanilido-6-methyl-1,4-oxathiin) (VITAVAX ®)
2,4-dichlorophenoxyacetic acid
-(4-chloro-2-methylphenoxy) butyric acid
2-(2,4-dichlorophenoxy) propionic acid
Ioxynil: 3,5 diiodo-4-hydroxybenzonitrile
Bromoxynil: 3,5 dibromo-4-hydroxybenzonitrile
Methoxychlor: 2,2,-Bis(p-methoxyphenyl)- 1,1-trichloroethane
PP 781: 4(2-chloro phenylhydrazono)-3-methyl-5-isoxazolone*
PP 675: 5-butyl-2-dimethylamino-4-hydroxy-6-methyl pyrimidine*
PP 062:5,6-dimethyl-2-dimethylamino-4 pyrimidinyl dimethylcarbamate*
PP 149:5-n-butyl-2 ethylamino-4-hydroxy-6 methyl-pyrimidine*
C 6313 N'-(4-bromo-3-chlorophenyl)-N-methoxy-N-methylurea
C 6989 2,4'dinitro-4-trifluoromethyl-diphenylether
Chloroxuron N'-4-(chlorophenoxy) phenyl-NN-dimethylurea
Dichlobenil 2,6-dichlorobenzonitrile
* Manufactured by Imperial Chemical Industries Limited
Diphenamid NN-dimethyl-2,2-diphenylacetamide
Fenac 2,3,6-trichlorophenylacetic acid
Fluomemron N'-(3-trifluoromethylphenyl)-NN-dimethylurea
GS 14260 4-ethylamino-2-methylthio-6-t-butyl-amino-1,3,5-triazine
PCP Pentachlorophenol
Lenacil 3-cyclohexyl-6,7-dihydro-1H-cyclo-pentapyrimidine-2,4-( 3 H,5H)-dione Pyrazon 5-amino-4-chloro-2-phenyl-3-pyridazone
Metrobromuron N'-(4-bromophenyl)-N-methoxy-N-methylurea
Metoxymarc N-(4-methoxybenzoyl)-N-(3,4-dichlorophenyl)-N',N '-dimethylurea
Neburon N-butyl-N'-(3,4-dichlorophenyl-N-methylurea
NIA 11092 1,1-dimethyl-3-[3-(n-t-butyl carbamyloxy)-phenyl]urea
Mecoprop 2-(4-chloro-2 methylphenoxy)propionic acid
Monolinuron N'-(4-chlorophenyl)-N-methoxy-N-methylurea
Nitrofen 2,4-dichlorophenyl 4-nitrophenylether
Propanil N-(3,4-dichlororphenyl)propionamide
Pyriclor 2,3,5-trichloro-4-pyridinol
Solan 3'-chloro-2-methyl-p-valerotoluidide
Terbacil 5-chloro-3-t-butyl-6-methyluracil
UC 22463 (SIRMATE)-3,4-dichlorobenzyl N-methylcarbamate
WL 9385 2-Azido-4-ethylamino-6-t-butylamino-s-triazine
Propachlor 2-chloro-N-isopropylacetanilide
CP 50144 2-chloro-N-2,6-diethylphenyl-N-methoxymethylacetamide
CP 31675 2-chloro-N-(2 methyl-6-t-butylphenyl)acetamide Prometryne 2-methylmercapto-4,6-bisisopropyl amino-s-triazine
DCPA dimethyl 2,3,5,6, tetrachloroterephthalate
Benerin N-buty 1-N-ethyl-2,2,2, trifluoro-2,6-dinitro-p-to luidine
Nitralin 2,6-dinitro-4-methylsulfonyl-N,N-dipropyl-aniline
PP 493 2,6-difluoro-3,5-dichloro-4-hydroxy pyridine
CNP 2,4,6-trichlorophenyl-4'-nitrophenyl ether
Pentachloro nitrobenzene
1-(butyl carbamoyl)-2-benzimidazole carbamic acid, methyl ester (BENLATE ®).
Carbaryl (methylnaphthyl carbamate) (active ingredient in Sevin).

The third group constitutes those compounds which are water-soluble, such as, salts, e.g., the isopropylamine salt of phosphonomethyl glycine, the sodium salt of 2,4-dichlorophenoxy acetic acid, the sodium salt of methoxy dichloro benzoic acid (dichloro anisic acid), and dicamba (dimethylamine salt of methoxy dichloro-benzoic acid), Assert bisulfate (American Cyanamid), the ammonium salt of imazaquin (American Cyanamid), and the like.

The following Examples illustrate the invention:

The materials used in the Examples and designated by trademark or tradename are as follows:

| | |
|---|---|
| Agrimer AL25 | copolymer of vinyl pyrrolidone and $C_{16}$ α-olefin in 50:50 weight ratio with a number average molecular weight of about 9500; |
| Agrimer AL30 | graft copolymer containing 80% by weight of $C_{20}$ α-olefin and 20% by weight of polymerized vinylpyrrolidone with a number average molecular weight of about 8600 available as a solid; |
| Agrimer AL22 | graft copolymer containing 80% by weight of $C_{16}$ α-olefin and 20% by weight of polymerized vinylpyrrolidone with a number average molecular weight of about 7300 available as a liquid; |
| Agrimer VA3 | copolymer containing 30 mole % vinylpyrrolidone units and 70 mole % vinylacetate unit with a number average molecular weight of 5700 and weight average molecular weight of 28,800 determined by the GPC method; |
| ACP-1004 | copolymer containing 50:50 weight ratio of the monomer with number average molecular weight = 30,000–60,000, 100,000–300,000. |
| Rodeo | a commercially available pesticide of an aqueous solution containing 53.8% of the isopropylamine salt of phosphonomethyl-glycine (a.i.-1) (Monsanto). |
| Latron B1956 | 77% modified phthalic glycol alkyl resin, and 23% inert ingredients including organic solvent (Rohm & Haas); |
| Prowl | an emulsion concentrate containing 42.0% by wt. pendimethalin (a.i.-2). The balance constitutes surfactants and solvents. |
| Roundup | a commercially available concentrate of glyphosate with suitable welling agents. Glyphosate is the isopropylamine salt of phosphonomethylglycine. |
| Gramoxone | a commercially available concentrate of Paraquat in suitable wetting agents. Paraquat is 1,1-dimethyl-4,4'-bipyridinium dichloride (American Cyanamid). |
| Alcasurf CA | a commercial form of calcium dodecyl benzene sulfonate produced by Rhone Poulenc containing an oil-soluble anionic surfactant (0.32 parts propylene glycol, 0.65 parts n-butanol, 3.90 parts calcium dodecyl benzene sulfonate and 1.62 parts of aromatic hydrocarbons). |
| Pendimethalin | N-(1-ethylpropyl)-3,4-dimethyl-2,6-dinitrobenzenamine. |
| Fusilade EC | a commercial formulation of the active ingredient butyl 2-[4-(5-trifluoromethyl-2-pyridyloxy)phenoxy]propionate (FUSILADE 2000) which is a selective systemic herbicide for control of grass weeds in broadleaved crops. |
| Thiadiazuron | N-phenyl-N'-1,2,4-thiadiazol-5-yi urea. |

Cypromid 3',4'-dichlorocyclopropane carboxanilide
Fenuron NN-dimethyl-N-phenylurea
Chlorbromuron N'-(4-bromo-3-chlorophenyl)-N-methoxy-N-methylurea
Ametryne 2-methy lmercapto-4-ethy lamino-6-isopropyl-amino-s-triazine In accordance with the present invention, emulsion concentrates (EC) may be prepared by mixing an active ingredient with a water-insoluble polymer in accordance with the invention and a solvent for the water-insoluble polymer. Such solvents can include aromatic diluents as well as long-chain alkyl pyrrolidones. These concentrates may then be diluted with water to provide stable emulsions. I have discovered that a stable emulsion can be prepared from such a concentrate without the presence of a water-soluble surfactant. Thus, in Example 1, comparison of a composition with an aromatic diluent and with and without a water-soluble surfactant is shown. In Example 2, the use of N-octyl pyrrolidone as a solvent is shown with and without the presence of a water-soluble surfactant. In each case, a stable macroemulsion could be obtained by dilution of the compositions without the water-soluble surfactant. In addition, as is shown in Example 3, the inventive emulsion concentrates provide excellent rainfastness with respect to retention of the active ingredient.

Examples 1 and 2 illustrate the preparation of inventive compositions wherein a solvent, e.g., an aromatic diluent or long-chain alkyl pyrrolidone, are used.

EXAMPLE 1

The compositions shown in Table 1 below were prepared by mixing the ingredients and shaking in an orbital shaker for 30 minutes to form homogeneous concentrates.

TABLE 1

| Ingredients | Weight (grams) | |
|---|---|---|
| | $I_A$ | $I_B$ |
| Pendimethalin | 21 | 21 |
| Exxon Aromatic 150 | 74 | 74 |
| Gafac RE 610 | — | 5 |
| AgriLiner AL 25* | 5 | — |

*AL 25 is commercially available as a 50 percent solution in isopropyl alcohol (IPA). It is used in these examples as a solid obtained by stripping the IPA by evaporation under vacuum below 65° C.

The emulsifiable concentrates $I_A$ and $I_B$ were evaluated for cold stability and the quality of the emulsion obtained on dilution to two percent with water. It is noted that this is the conventional dilution rate for use in the field. The results are shown in Table 1A.

TABLE 1A

| FREEZE STABILITY OF Pendimethalin EC* | | |
|---|---|---|
| Formula # (EC) | $I_A$ | $I_B$ |
| Time 24 hrs | no crystals | no crystals |
| 48 hrs | no crystals | no crystals |

*measured at 2° ± 1° C.

The emulsions were evaluated to determine the amount of active ingredient which could be recovered. For this purpose, 50 g of the emulsions obtained on dilution of the compositions $I_A$ and $I_B$ were introduced to a long Nessler tube. 1 g aliquots of samples were withdrawn from the middle of the tube periodically, diluted with ethanol 1/500 times and UV spectra were taken. The absorbance at 238.5 nm ($\lambda$ max. i.e., the wavelength corresponding to maximum absorbance) was measured and calibration data for absorbance versus concentrations was obtained using standard solutions. Using a least squares line (absorbance =0.08058×concentration (ppm)+0.0008785), the amount of active ingredient present in the sample taken from the Nessler tube was evaluated over a period of 24 hours. A constant recovery rate of 100% was obtained for each of compositions $I_A$ and $I_B$.

The above diluted emulsion concentrate (Ec) $I_A$ and $I_B$ were evaluated for emulsion stability on standing. Formation of foam, solid, cream, oil and crystal formation upon microscopic examination were observed. The emulsion was passed through various mesh screens to separate any crystals formed which were observed under 250× magnification. The results are shown in Table 1B hereinafter.

TABLE 1B

| EMULSION EVALUATION OF PENDIMETHALIN EC ON STANDING | | | | |
|---|---|---|---|---|
| Formula | $I_A$ | | $I_B$ | |
| Dilution | 1 g EC/50 g hard water | | 1 g EC/50 g hard water | |
| % Pendimethalin | 0.42% | | 0.42% | |
| 0 time | no emulsion oil stayed on top | | partial emulsion half way down the tube | |
| After 20 Inversions | translucent macroemulsion | | macroemulsion | |
| Key: | Top | Bottom | Top | Bottom |
| foam 0 hr | 0 | 0 | f10 | 0 |
| solid 1 hr | f5 | 0 | C5 | 0 |
| cream* 2 hr | C6 | 0 | C6 | 0 |
| oil* 4 hr | C7 | 0 | C7 | 0 |
| 6 hr | C7 | 0 | C7 | 0 |
| 24 hr | C7 | 0 | C10 | 0 |
| 24 hr microscope 250X mesh | | | | |
| 60 | 0 | | 0 | |
| 100 | 0 | | 0 | |
| 250 | 0 | | + | |

*As used herein, the oil means a clear layer and cream means a cloudy layer of solid and oil.

Table 1C shows the formation of crystals for compositions $I_A$ and $I_B$ over a period of time.

TABLE 1C

| CRYSTAL FORMATION OBSERVATIONS FOR PENDIMETHALIN EC MICROSCOPE 250X | | |
|---|---|---|
| | $I_A$ | $I_B$ |
| Dilution | 1 g/50 g hard water | 1.5 g/50 g hard water |
| 0-Time | none observed | 50 crystals per view |
| 1 hr | none observed | none observed |
| 2 hr | none observed | — |
| 4 hr | none observed | 10 crystals per view |
| 6 hr | none observed | 1 crystal per 80 view |
| 24 hr | none observed | 1 crystal per 30 view |
| Average size crystal | — | 3 × 7 micron |
| Filtered | | |
| 60 mesh | 0 | 0 |
| 100 mesh | 0 | 0 |
| 250 mesh | 0 | 0 |

EXAMPLE 2

Compositions were prepared using the procedure of Example 1 and the following ingredients:

TABLE 2

| Ingredients | Weight (grams) | |
|---|---|---|
| | $II_A$ | $II_B$ |
| Thiadiazuron | 10 | 10 |
| Agsol Ex 8 (N-octylpyrrolidone) | 80 | 80 |
| Agrimer AL 35 | 5 | — |
| Gafac RE 610 | — | 5 |

The emulsifiable concentrates were evaluated for quality of emulsion on dilution. These results obtained using the same procedure as for compositions $I_A$ and $I_B$ are shown in Table 2A and 2B.

TABLE 2A

EMULSION EVALUATION OF Thiadiazuron EC ON STANDING

| Formula # | II$_A$ | | II$_B$ | |
|---|---|---|---|---|
| Dilution | 1 g/50 ml | 1 g/50 ml | 1 g/50 ml | 1 g/50 ml |
| Diluted with | DI H$_2$O | WHO | DI H$_2$O | WHO |
| % Thiadiazuron | 0.2% | 0.2% | 0.2% | 0.2% |
| After 20 Inversions | emulsion | emulsion | emulsion | emulsion |
| Key | T    B | T    B | T    B | T    B |
| foam 0 min. | 9    0 | 7    0 | 41    0 | 38    0 |
| solid 30 min. | 0    0 | 0    0 | 30    0 | 0    0 |
| cream 1 hour | õ1    0 | õ2    0 | 0    0 | õ1    0 |
| oil 2 hr | õ1    0 | õ5    0 | C1    0 | õ2    0 |
| E = separated emulsion #: mm | | | | |
| 4 hr | õ2    0 | õ6    0 | C6    0 | õ5    0 |
| 6 hr | õ3    S1 | õ6    S2 | C6    0 | õ5    0 |
| 8 hr | õ3    S1 | õ6    S2 | C6    0 | õ5    0 |
| 24 hr | õ5    S1 | õ5    S2 | C7    0 | õ5    E 50 |
| filtered mesh | | | | |
| 60 | 0 | 0 | 0 | 0 |
| 100 | 0 | 0 | 0 | + |
| 250 | 0 | 0 | + | + |

T = Top; B = Bottom

TABLE 2B

CRYSTAL FORMATION OBSERVATIONS FOR THIADIAZURON EC MICROSCOPE 250X

| Formula # | II$_A$ | II$_B$ |
|---|---|---|
| Dilution | 2 g/100 g hard water | 2 g/100 g hard water |
| 0-Time | none observed | none observed |
| 1 hr | none observed | none observed |
| 2 hr | none observed | none observed |
| 4 hr | none observed | none observed |
| 6 hr | none observed | none observed |
| 24 hr | none observed | none observed |
| Average Size crystal | | |

Stirred Emulsion

As shown, a stable emulsion on dilution with water can be obtained with the inventive emulsion concentrate without the use of a water-soluble surfactant.

EXAMPLE 3

Rainfastness evaluations were carried out for polymer films formed in accordance with the invention. These evaluations were carried out using compositions prepared from commercially available formulations. Such formulations conventionally are composed of an agriculturally active chemical (the active ingredient), surfactants and organic diluents as solvents. Consequently, with such commercial formulations, simply by adding the water insoluble polymer in accordance with the present invention, one can obtain the emulsion concentrate of the invention, the solvent and surfactant being present. It is noted that while the surfactant is already present in the commercial formulation as obtained and, consequently, cannot be removed, it is actually not necessary when used with the water-insoluble polymer according to the invention. However, its presence does not adversely affect the ability to produce a significant improvement in the rainfastness of the commercial formulation.

The general procedure used was as follows:
1. A commercial formulation of a given agriculturally active ingredient was admixed with a film-forming water-insoluble polymer.
2. The liquid mixture was then diluted to end use concentrations. An appropriate dose (0.1 g to 0.5 g) was uniformly applied to a 6"×6" glass plate uniformly as a 1–3" square patch. The patch was dried in a hood under ambient conditions for 48–72 hours. (3 samples were tested for each formulation.)
3. After a dry film was formed, a fine spray of water was applied to simulate 0.5–2 inches of rain wash-off. The washings were collected in a waste jar.
4. The remaining washed patch was extracted with a solvent (ethanol is preferred) quantitatively into a 100 ml volumetric flask. If desired, appropriate dilutions of the ethanol extract were made.
5. The ethanol extract was subjected to ultraviolet spectra examination and the absorbance at a λ max was determined (this value is designated $X_1$).
6. Blank samples of compositions III$_A$, III$_B$, III$_C$, III$_D$, III$_E$, III$_F$, and III$_G$ were obtained by diluting each in ethanol to yield a solution containing 8 ppm of the active ingredient. The UV absorption of each was measured. These values were utilized to prepare a calibration chart. This value is designated $X_2$.
7. The percent retained was then determined by dividing $X_1$ by $X_2$ and multiplying by 100.
8. Blanks of the commercial formulations without polymer were run under identical conditions. The percentage was calculated.
9. For samples wherein the pesticide used is Pendimethalin, λ max. is 239 nm. 0.3 g of diluted samples were used for patches (1–2 square inches). The amount of wash-off water used was 1.5 to 2.5 g.

In all examples using an aromatic oil in the formulations, samples of the alcohol extract from the dried spot after the rain wash were completely evaporated in a vacuum oven to remove any residual aromatic solvent so as to avoid interference therefrom in the absorbance analysis.

Using the above general procedure, rainfastness evaluations for commercial pendimethalin formulations using Prowl as a commercially available emulsifiable concentrate of this active ingredient. This commercial formulation contains 42.0% of the active ingredient with the balance being surfactants and organic solvents. The compositions used were as follows:

Composition III$_A$—1 g of Prowl was diluted with 100 ml of D.I. water to provide an end use composition containing 0.42% active ingredient.

Composition III$_B$—90 parts of Prowl were mixed with solid Agrimer AL 25 (10 parts). 1 g of this mixture was diluted to 100 parts with D.I. water.

Composition III$_C$—The formulation of I$_A$ (1 g diluted to 50 g with D.I. water).

Composition III$_D$—The formulation of I$_B$ (1 g diluted to 50 g with D.I. water).

Composition III$_E$—This composition was the same as III$_B$ except that Agrimer VA3 was used in place of Agrimer AL 25. Agrimer VA 3 is commercially available as a 50% solution in ethanol. In these examples, it was used in solid form obtained by stripping the ethanol from the solution under vacuum at low temperature—under 65° C.). The resulting composition was obtained by diluting 1 g to 100 ml with D.I. water.

Composition III$_F$—90 parts of Prowl were mixed with 10 parts of solvent-stripped Latron B1956. 1 g of this composition was diluted to 100 g with D.I. water.

Composition III$_G$—The composition was the same as composition III$_B$ except that Agrimer AL 25 was replaced with Agrimer AL 30.

The results of the rainfastness formulations are shown in Table 3.

TABLE 3

| Composition | Spotted Sample | Contents | Weight Sample g | Appearance | Rain Wash Water (g) | Vol. EtoH Used ml | Absorbance | % Relative Rainfastness |
|---|---|---|---|---|---|---|---|---|
| II$_{A-1}$ (blank) | 1 | commercial | 0.3003 | slightly | 1.46 | 1/100 | 0.648 | 56.9 |
|  | 2 | pendimethalin | 0.3021 | beaded film | 1.48 | 1/100 | 0.530 | 46.2 |
|  | 3 | (Prowl) No Agrimer | 0.3008 | (1" dia. surface area) | 1.50 | 1/100 | 0.654 | 57.3 |
|  |  |  |  |  |  |  |  | 53.5 ± 6 |
| III$_B$ | 1 | commercial | 0.3064 | clear, even | 1.48 | 1/100 | 0.993 | 95.6 |
|  | 2 | pendimethalin | 0.3018 | film | 1.66 | 1/100 | 0.986 | 96.5 |
|  | 3 | (Prowl) + | 0.3020 | (4" dia.) | 1.54 | 1/100 | 0.986 | 96.4 |
|  | 4 | Agrimer AL 25 (0.1%) | 0.3039 |  | 1.55 | 1/100 | 0.990 | 96.4 |
|  |  |  |  |  |  |  |  | 96.2 ± 0.4 |
| III$_D$ | 1 | pendimethalin | 0.3028 | clear beaded | 1.47 | 1/50 | 0.255 | 13.6 |
|  | 2 | (a.i) | 0.3065 | film | 1.44 | 1/50 | 0.295 | 15.2 |
|  | 3 | Gafac RE 610 ÷ | 0.3020 | (4" diameter) | 1.51 | 1/50 | 0.406 | 21.5 |
|  | 4 | solvent | 0.3021 |  | 1.52 | 1/50 | 0.239 | 12.8 |
|  |  |  |  |  |  |  |  | 15.8 ± 4 |
| III$_C$ | 1 | pendimethalin | 0.3008 | clear even | 1.50 | 1/100 | 79.0 |  |
|  | 2 | + | 0.2996 | film | 1.51 | 1/100 | 92.9 |  |
|  | 3 | Agrimer AL25 + | 0.3075 | (4" diameter) | 1.51 | 1/100 | 92.9 |  |
|  | 4 | solvent (no surfactant) | 0.3060 |  | 1.52 | 1/100 | 82.0 | 86.7 ± 7 |
| III$_E$ VA 3 | 1 | Prowl + | 0.3062 | uneven | 1.57 | 1/100 | 0.919 | 85.5 |
|  | 2 | Agrimer VA 3 | 0.3028 | dry | 1.58 | 1/100 | 0.903 | 85.0 |
|  | 3 | (0.1%) | 0.3030 | film | 1.56 | 1/100 | 0.986 | 92.7 |
|  |  |  |  |  |  |  |  | 87.7 ± |
| III$_F$ | 1 | Prowl + solvent | 0.3516 | beaded film | 2.31 | 1/100 | 0.612 | 53.6 |
|  | 2 | stripped Lation | 0.3169 |  | 2.36 | 1/100 | 0.487 | 47.3 |
|  | 3 | B1956 (0.1%) | 0.3189 |  | 2.31 | 1/100 | 0.616 | 59.2 |
|  |  |  |  |  |  |  |  | 53.4 ± 6 |
| III$_G$ | 1 | Prowl + | 0.3457 | drug residue | 2.36 | 1/100 | 0.796 | 70.6 |
|  | 2 | Agrimer AL 30 | 0.3330 | unevenly | 2.29 | 1/100 | 0.738 | 67.9 |
|  | 3 | (1%) | 0.3309 | spread | 2.33 | 1/100 | 0.803 | 74.3 |
|  |  |  |  |  |  |  |  | 70.9 ± 3 |
| III$_{A-2}$ (blank)* | 1 | Prowl | 0.3287 | beaded un- | 2.30 | 1/100 | 0.320 | 25.3 |
|  | 2 | (no agrimer) | 0.322 | even film | 2.25 | 1/100 | 0.245 | 19.8 |
|  | 3 |  | 0.3074 |  | 2.28 | 1/100 | 0.299 | 25.3 |
|  |  |  | 0.3167 |  | 2.31 | 1/100 | 0.256 | 21.0 |
|  |  |  |  |  |  |  |  | 22.9 ± 3 |

*For comparison with III$_F$ and III$_G$.

To test the validity of the procedure, compositions III$_A$, III$_B$, III$_C$, III$_D$, III$_E$, III$_F$, and III$_G$ were diluted in ethanol to yield a solution containing 8 ppm of the active ingredient. The UV absorbance was measured at λ max. and all values (concentration of active ingredient) were within ±2% of the theoretical values.

EXAMPLE 4

The following compositions were prepared:
Composition IV$_A$—identical to composition III$_A$
Composition IV$_B$—same as composition III$_B$ except that 2 pans of Agrimer AL 25 were mixed with 98 pans of Prowl and 1 g of this mixture was diluted to 100 g with D.I. water.
Composition IV$_C$—This was the same as composition III$_B$ except 5 pans of Agrimer AL 25 were mixed with 95 parts of Prowl.

The rainfastness was evaluated using the experimental procedure of Example 3. The percent of active ingredient recovered from the formulations is shown in Table 4.

TABLE 4

| Compositions | % Agrimer AL 25 in the final dilution | % a.i. recovered |
|---|---|---|
| IV$_A$ | 0 | 54.7 ± 6 |
| IV$_B$ | 0.02 | 77.2 ± 2 |

TABLE 4-continued

| Compositions | % Agrimer AL 25 in the final dilution | % a.i. recovered |
|---|---|---|
| IV$_C$ | 0.05 | 80.1 ± 7 |

EXAMPLE 5

The following formulations were prepared:
Composition V$_A$—14.61 g of dried Agrimer AL 25 were dissolved in 64.29 g of Exxon Aromatic 150, 14.61 g N-octyl pyrrolidone were added, followed by the addition of 6.49 g of a surfactant, Alcasurf CA. The mixture was stirred for 40 minutes in an orbital shaker to produce a clear solution. The composition can also be prepared by using 29.2 g of a 50% isopropyl alcohol solution of the polymer (Agrimer AL 25) and 14.61 g of N-octylpyrrolidone with 64.3 g of Exxon Aromatic 150 (or other higher boiling diluents). The isopropyl alcohol may be separated by evaporation under atmospheric or reduced pressure. 6.49 g Alcasurf CA, is then added to produce 100 g of the inventive composition.

Composition V$_B$—14.6 g of Agrimer AL 30 were dissolved in 14.6 g of N-octyl pyrrolidone, 64.3 g of Exxon aromatic 150 and 6.5 g of Alcasurf CA. The mixture was stirred for 30 minutes to produce a clear solution.

Composition V$_C$—15 g of Agrimer AL 25 (solvent-stripped) were dissolved in 85 g of Exxon aromatic 150.

Composition V_D—This composition was the same as composition V_C except that the Agrimer AL 25 was replaced by an equivalent amount of Agrimer AL 30 (solvent-stripped).

(The above-noted compositions are depicted in Table 5)

TABLE 5

% WEIGHT COMPOSITIONS OF SOLVENT BASED POLYMER COMPOSITIONS:

| Ingredients | $V_A$ | $V_B$ | $V_C$ | $V_D$ |
|---|---|---|---|---|
| N-octylpyrrolidone | 14.6 | 14.6 | — | — |
| Exxon Aromatic 150 | 64.3 | 64.3 | 85 | 85 |
| Ethanol | — | — | — | — |
| Agnmer AL25 | 14.6 | — | 15 | — |
| Agriiner AL 30 | — | 14.6 | — | 15 |
| Alcasurf CA | 6.5 | 6.5 | — | — |
| Total | 100.0 | 100.0 | 100 | 100 |

Compositions $V_A$ and $V_B$ were diluted with D.I. water or 342 ppm hard water to produce stable emulsions at dilution rates of 1/10, 1/20, 1/50, 1/100 and 1/1000. The emulsions produced from composition $V_A$ were more stable than those from composition $V_B$. Hard water produced more stable emulsions than D.I. water. Formulation of stable emulsions in water makes it possible to use the above compositions in both oil based and water based active ingredient formulations. It is noted that compositions $V_A$ and $V_B$ are particularly advantageous for use in oil base active ingredient concentrates in aqueous medium.

EXAMPLE 6

Rainfast evaluations using the procedure of Example 3 hereinabove were carried out for compositions $V_A$, $V_B$, $V_C$, and $V_D$ as well as at Latron B 1956 for comparison purposes. The compositions used were as follows:

Composition VI blank This was essentially the same as composition III_A.

Composition VI_A—1 g of Prowl was mixed with 0.67 g of composition $V_A$ and then diluted to 100 g with D.I. water.

Composition VI_B—1 g of Prowl was mixed with 0.67 g of composition $V_B$ and then diluted to 100 g with D.I. water.

Composition VI_C—1 g of Prowl was mixed with 0.67 g of composition $V_C$ and then diluted to 100 g with D.I. water.

Composition VI_D—1 g of Prowl was mixed with 0.67 g of composition $V_D$ and then diluted to 100 g with D.I. water.

Formulations VI blank, VI_A, VI_B, VI_C and VI_D were evaluated for rainfastness of the pendimethalin using 0.32–0.34 g for spotting and 2.2 to 2.4 g of wash water to simulate rain. The evaluation showed that formulations VI_A, VI_B, VI_C and VI_D exhibited increased retention of the active ingredient as compared to the blank. The effectiveness was in the following decreasing order:

$VI_A(38.7\pm6) > VI_B(30\pm1) > VI_D(23\pm4) > VI_C(19.4\pm3) > VI(12\pm1)$

The foregoing represent the averages of three runs for each composition.

In the above experiment, the pump spray equipment used, i.e., force of spray, to simulate rain was different from the procedure outlined in Example 3. This could explain the lower retention.

The evaluation of Latron B1956 as a tank mix additive showed that the inventive formulations produced 60 to 80% higher retention at the same level of application as the Latron B1956 containing composition.

EXAMPLE 7

A series of formulations was prepared containing commercial carbaryl (Sevin) and evaluated for rainfastness. Sevin is a formulation containing 27% of carbaryl as an active ingredient. The compositions were as follows:

Composition VII blank 1 g of commercial Sevin was diluted to 200 g with D.I. water to produce an emulsion of about 0.14% active ingredient.

Composition VII_A—Same composition as VII blank except that 0.27 g of composition $V_A$ was added prior to dilution.

Composition VII_B—Same composition as VII_A except that 0.67 g of composition $V_A$ were added.

Composition VII_C—Same composition as VII_A except that composition $V_A$ was replaced with composition $V_B$.

Composition VII_D—Same as composition VII_B except that composition $V_A$ was replaced by composition $V_B$.

Composition VII_E—Same as composition VII_B except that composition $V_A$ was replaced by composition $V_C$.

Composition VII_F—Same as composition VII_B except that composition $V_A$ was replaced by composition $V_D$.

These formulations were evaluated using the same procedure as set for in Example 3. Specifically, 0.45–0.54 g of the sample were spotted onto glass plates and 1.5–1.7 g of water was used to simulate rain wash. The λ max. used for the evaluation was 279 nm and the least square line was used according to the following formula:

absorbance = 0.03276 × concentration (ppm) − 0.016416.

The results of the evaluations are shown in Table 6.

TABLE 6

SUMMARY RESULTS OF RAINFASTNESS FOR CARBAMYL ("SEVIN") FORMULATIONS

| COMPOSITION | % AGRIMER | % A.I. RECOVERED |
|---|---|---|
| VII (blank) | 0 | 39.2 ± 4 |
| VI_A | Agrimer AL 25 (0.02%) | 55.4 ± 7 |
| VII_B | Agrimer AL 25 (0.05%) | 59 ± 8 |
| VII_C | Agrimer AL 30 (0.05%) | 63 ± 7 |
| VII_D | Agrimer AL 30 (0.05%) | 62 ± 9 |
| VII_E | Agrimer AL 25 (0.05%) | 56 ± 6 |
| VII_F | Agrimer AL 30 (0.05%) | 59.6 ± 8 |

EXAMPLE 8

It is noted that formulation $V_A$ is particularly useful as an adjuvant for oil based concentrates. Such oil based concentrates (concentrates based on a nonaqueous hydrophobic solvent) normally are composed of:

active ingredients—10 to 60 percent;

surfactants (wetting agents and emulsifiers)—1 to 30 percent;

hydrophobic non-aqueous solvents—10 to 80 percent; and optionally, defoamers, rheology modifiers and the like as needed 0 to 5 percent.

It exhibits enhanced efficacy with the active ingredient Fusilade EC when used at a 0.2% concentration in the final dilution. Also, increased biological activity with chloropyrifos, an insecticide, was observed when composition $V_A$ was used with an oil based concentrate for this active ingredient at a 0.2% concentration in the final dilution.

EXAMPLE 9

The compositions of the present invention, for example, Compositions $V_A$ and $V_B$ can be used as granulating fluids to incorporate the water-insoluble polymers in solid water-dispersible granular formulations. A typical formulation is as follows:

| | |
|---|---|
| Active ingredient (Atrazine) | 82.3% by weight |
| Binder (polyvinyl pyrrolidone - optional) | 3.0 |
| Dispersant | 3.0 |
| Wetting agent | 1.5 |
| Defoamer | 0.2 |
| Composition $V_A$ or $V_B$ | 10.0 |

Typical examples of the dispersants, wetting agents, and defoamers are: Morwet D-425, alkylated naphthalene sulfonate sodium salt, Morwet EFW which is a proprietary mixture of sulfated alkylcarboxylate and a sulfonated alkylnaphthalene sodium salt, and FOAMASTER soap L which is a proprietary soda soap.

In such a composition, the aromatic oil diluent can be dispensed with. The water-dispersible granules are prepared by charging the weight ingredients (200 g) in a V-blender and mixing for 10 to 30 minutes. The charge is then loaded to a 24 inch pan granulator set at an angle of 50° to 55°. The pan is rotated at a speed of 15 rpm and granulation is accomplished by spraying the charge with water at an appropriate speed, typically, 20 to 30 ml of water is used over a period of 10 to 30 minutes. After granulation, the wet granules are dried at 40° to 50° C. to reduce the moisture level to about 1 to 2%. The dry granules can be sieved to segregate them into different size fractions as desired. Undersized granules can be reformulated by recycling to the process. The granules can also be prepared by using a conventional extrusion process with a suitable extruder.

What is claimed is:

1. An emulsion concentrate comprising:
   a) 2 to 90% by weight of a solvent selected from the group consisting of long-chain alkylpyrrolidones, synthetic or naturally occurring hydrophobic oils, and mixtures thereof;
   b) 1 to 60% by weight of a water-insoluble graft polymer of N-vinylpyrrolidone and an α-olefin selected from the group consisting of $C_{16}$ α-olefins in a 50:50 weight ratio and $C_{20}$ α-olefins in a 20:80 weight ratio and
   c) 1 to 85% by weight of an oil-soluble surfactant.

2. The emulsion concentrate of claim 1 wherein the solvent is a long-chain alkylpyrrolidone having the formula

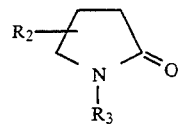

wherein $R_2$ is hydrogen or alkyl having from 6 to 14 carbon atoms and $R_3$ is alkyl having from 6 to 14 carbon atoms with the proviso that at least one of $R_2$ or $R_3$ must contain at least 6 carbon atoms and the sum of the carbon atoms in $R_2$ and $R_3$ cannot exceed 14, or the solvent is a synthetic or naturally occurring oil having a hydrophobic character or having a fractional dispersive solubility parameter of greater than 70%.

3. The emulsion concentrate of claim 2 wherein $R_2$ is hydrogen and $R_3$ is $C_8$ or $C_{12}$.

4. The emulsion concentrate of claim 2 which further contains N-methylpyrrolidone.

5. The emulsion concentrate of claim 2 wherein the solvent is selected from the group consisting of soybean oil, rapeseed oil, long chain alcohols, long chain ketones, long chain esters, ethers, aromatic petroleum oils composed of heavy aromatic solvent naphtha—about 60%; middle distillate solvent extractant—about 40%, and combinations thereof.

6. The emulsion concentrate of claim 1 wherein the α-olefin contains from 8 to 30 carbon atoms.

7. The emulsion concentrate of claim 1 comprising from about 2 to 90 weight percent of a solvent selected from the group consisting of N-octylpyrrolidone, a crude oil distillate having an average boiling point of at least 120° C. and mixtures thereof, from about 1 to 60 weight percent of a copolymer of N-vinylpyrrolidone and a $C_{16}$α-olefin in a 50:50 weight ratio and a number average weight of about 9500.

8. The emulsion concentrate of claim 1 wherein the solvent is selected from the group consisting of N-octylpyrrolidone, N-methylpyrrolidone, a crude oil distillate having an average boiling point of at least 120° C., and mixtures thereof.

9. The concentrate of claim 1 wherein the solvent is selected from the group consisting of 10–20% by weight N-octylpyrrolidone, 50–70% by weight of the hydrophobic oils, and mixtures thereof, the water-soluble polymer is present in an amount from 10 to 20% by weight and the oil-soluble surfactant is present in the amount from 5 to 10% by weight.

10. The concentrate of claim 1 wherein the solvent is a long-chain alkylpyrrolidone.

11. A method for producing a water-dispersible granule of an agriculturally active ingredient comprising charging an agriculturally active ingredient and the emulsion concentrate of claim 1 to a granulator to form granules, and drying the granules.

12. The emulsion concentrate of claim 1 which further comprises an effective amount of an agriculturally active chemical.

13. A composition for application to agricultural crops comprising an emulsion of the emulsion concentrate of claim 12 diluted at least 2-fold with water.

14. A method for treating crops comprising applying the composition of claim 13 to the crops.

15. A method for treating crops comprising mixing the granules of claim 14 with water to form an emulsion and applying the emulsion to the crops.

16. Granules obtained by the method claim 13.

* * * * *